United States Patent
Garvey et al.

(10) Patent No.: US 10,314,667 B2
(45) Date of Patent: Jun. 11, 2019

(54) CLEANING DEVICE FOR CLEANING MEDICAL INSTRUMENT

(71) Applicant: Covidien LP, Mansfield, MA (US)

(72) Inventors: Zachary Garvey, Stillwater, MN (US); Lucas Schneider, Champlin, MN (US); Ethan Guggenheimer, Minnetonka, MN (US)

(73) Assignee: Covidien LP, Mansfield, MA (US)

( * ) Notice: Subject to any disclaimer, the term of this patent is extended or adjusted under 35 U.S.C. 154(b) by 444 days.

(21) Appl. No.: 15/076,102

(22) Filed: Mar. 21, 2016

(65) Prior Publication Data

US 2016/0278876 A1 Sep. 29, 2016

Related U.S. Application Data

(60) Provisional application No. 62/137,887, filed on Mar. 25, 2015.

(51) Int. Cl.
*A61B 90/70* (2016.01)

(52) U.S. Cl.
CPC ........ *A61B 90/70* (2016.02); *A61B 2090/701* (2016.02)

(58) Field of Classification Search
CPC ..... A61B 90/70; A61B 2090/701; A61L 2/18; A61M 2025/0019; B08B 3/04; B08B 1/00; B08B 9/02
USPC .......................................... 134/169 C, 166 C
See application file for complete search history.

(56) References Cited

U.S. PATENT DOCUMENTS

| | | | |
|---|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |

(Continued)

FOREIGN PATENT DOCUMENTS

| CA | 2000621 | 4/1990 |
|---|---|---|
| DE | 3732236 C1 | 12/1988 |

(Continued)

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(Continued)

*Primary Examiner* — David G Cormier
*Assistant Examiner* — Thomas Bucci

(57) ABSTRACT

A cleaning device for cleaning a medical instrument. First and second body portions in a closed position define a flushing chamber. The medical instrument extends through the flushing chamber. First and second sealing members secured to the first and second body portions engage one another to seal the flushing chamber and engage the medical instrument to form a seal thereabout. Portions of at least the first sealing member are disposed within the flushing chamber. Positive pressure in the flushing chamber urges the first sealing member toward the second and toward the medical instrument to enhance the tightness of the flushing chamber seal.

20 Claims, 11 Drawing Sheets

(56) References Cited

U.S. PATENT DOCUMENTS

| | | |
|---|---|---|
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,622 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,889,061 A | 12/1989 | McPherson et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |

(56) References Cited

U.S. PATENT DOCUMENTS

| | | |
|---|---|---|
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |

(56) References Cited

U.S. PATENT DOCUMENTS

| | | | |
|---|---|---|---|
| 5,711,921 A * | 1/1998 | Langford | A61B 1/123 134/169 R |
| 5,713,913 A | 2/1998 | Lary et al. | |
| 5,715,825 A | 2/1998 | Crowley | |
| 5,716,410 A | 2/1998 | Wang et al. | |
| 5,720,735 A | 2/1998 | Dorros | |
| 5,724,977 A | 3/1998 | Yock et al. | |
| 5,728,123 A | 3/1998 | Lemelson et al. | |
| 5,733,296 A | 3/1998 | Rogers et al. | |
| 5,735,816 A | 4/1998 | Lieber et al. | |
| 5,741,270 A | 4/1998 | Hansen et al. | |
| 5,753,195 A * | 5/1998 | Langford | A61B 1/123 134/169 R |
| 5,755,894 A | 5/1998 | Bowman et al. | |
| 5,766,192 A | 6/1998 | Zacca | |
| 5,772,674 A | 6/1998 | Nakhjavan | |
| 5,775,327 A | 7/1998 | Randolph et al. | |
| 5,776,114 A | 7/1998 | Frantzen et al. | |
| 5,776,153 A | 7/1998 | Rees | |
| 5,779,643 A | 7/1998 | Lum et al. | |
| 5,779,673 A | 7/1998 | Roth et al. | |
| 5,779,721 A | 7/1998 | Nash | |
| 5,779,722 A | 7/1998 | Shturman et al. | |
| 5,792,157 A | 8/1998 | Mische et al. | |
| 5,797,949 A | 8/1998 | Parodi | |
| 5,799,655 A | 9/1998 | Jang et al. | |
| 5,807,329 A | 9/1998 | Gelman | |
| 5,810,867 A | 9/1998 | Zarbatany et al. | |
| 5,816,923 A | 10/1998 | Milo et al. | |
| 5,820,592 A | 10/1998 | Hammerslag | |
| 5,823,971 A | 10/1998 | Robinson et al. | |
| 5,824,039 A | 10/1998 | Piplani et al. | |
| 5,824,055 A | 10/1998 | Spiridigliozzi et al. | |
| 5,827,201 A | 10/1998 | Samson et al. | |
| 5,827,229 A | 10/1998 | Auth et al. | |
| 5,827,304 A | 10/1998 | Hart | |
| 5,827,322 A | 10/1998 | Williams | |
| 5,830,224 A | 11/1998 | Cohn et al. | |
| 5,836,957 A | 11/1998 | Schulz et al. | |
| 5,843,022 A | 12/1998 | Willard et al. | |
| 5,843,103 A | 12/1998 | Wulfman | |
| 5,843,161 A | 12/1998 | Solovay | |
| 5,855,563 A | 1/1999 | Kaplan et al. | |
| 5,865,748 A | 2/1999 | Co et al. | |
| 5,868,685 A | 2/1999 | Powell et al. | |
| 5,868,767 A | 2/1999 | Farley et al. | |
| 5,871,536 A | 2/1999 | Lazarus | |
| 5,873,882 A | 2/1999 | Straub et al. | |
| 5,876,414 A | 3/1999 | Straub | |
| 5,879,397 A | 3/1999 | Kalberer et al. | |
| 5,883,458 A | 3/1999 | Sumita et al. | |
| 5,888,201 A | 3/1999 | Stinson et al. | |
| 5,895,399 A | 4/1999 | Barbut et al. | |
| 5,895,402 A | 4/1999 | Hundertmark et al. | |
| 5,902,245 A | 5/1999 | Yock | |
| 5,910,150 A | 6/1999 | Saadat | |
| 5,911,734 A | 6/1999 | Tsugita et al. | |
| 5,916,210 A | 6/1999 | Winston | |
| 5,922,003 A | 7/1999 | Anctil et al. | |
| 5,935,108 A | 8/1999 | Katoh et al. | |
| 5,938,645 A | 8/1999 | Gordon | |
| 5,938,671 A | 8/1999 | Katoh et al. | |
| 5,938,672 A | 8/1999 | Nash | |
| 5,941,869 A | 8/1999 | Patterson et al. | |
| 5,947,985 A | 9/1999 | Imran | |
| 5,948,184 A | 9/1999 | Frantzen et al. | |
| 5,951,480 A | 9/1999 | White et al. | |
| 5,951,482 A | 9/1999 | Winston et al. | |
| 5,954,745 A | 9/1999 | Gertler et al. | |
| 5,968,064 A | 10/1999 | Selmon et al. | |
| 5,972,019 A | 10/1999 | Engelson et al. | |
| 5,979,951 A | 11/1999 | Shimura | |
| 5,985,397 A | 11/1999 | Witt et al. | |
| 5,989,281 A | 11/1999 | Barbut et al. | |
| 5,997,557 A | 12/1999 | Barbut et al. | |
| 6,001,112 A | 12/1999 | Taylor | |
| 6,010,449 A | 1/2000 | Selmon et al. | |
| 6,010,522 A | 1/2000 | Barbut et al. | |
| 6,013,072 A | 1/2000 | Winston et al. | |
| 6,016,649 A | 1/2000 | Bock et al. | |
| 6,019,778 A | 2/2000 | Wislon et al. | |
| 6,022,362 A | 2/2000 | Lee et al. | |
| 6,027,450 A | 2/2000 | Brown et al. | |
| 6,027,460 A | 2/2000 | Shturman | |
| 6,027,514 A | 2/2000 | Stine et al. | |
| 6,032,673 A | 3/2000 | Savage et al. | |
| 6,036,646 A | 3/2000 | Barthe et al. | |
| 6,036,656 A | 3/2000 | Slater | |
| 6,036,707 A | 3/2000 | Spaulding | |
| 6,039,693 A | 3/2000 | Seward et al. | |
| 6,048,349 A | 4/2000 | Winston et al. | |
| 6,050,949 A | 4/2000 | White et al. | |
| 6,063,093 A | 5/2000 | Winston et al. | |
| 6,066,153 A | 5/2000 | Lev | |
| 6,068,603 A | 5/2000 | Suzuki | |
| 6,068,638 A | 5/2000 | Makower | |
| 6,081,738 A | 6/2000 | Hinohara et al. | |
| RE36,764 E | 7/2000 | Zacca et al. | |
| 6,095,990 A | 8/2000 | Parodi | |
| 6,099,542 A | 8/2000 | Cohn et al. | |
| 6,106,515 A | 8/2000 | Winston et al. | |
| 6,110,121 A | 8/2000 | Lenker | |
| 6,120,515 A | 9/2000 | Rogers et al. | |
| 6,120,516 A | 9/2000 | Selmon et al. | |
| 6,126,649 A | 10/2000 | VanTassel et al. | |
| 6,129,734 A | 10/2000 | Shturman et al. | |
| 6,134,003 A | 10/2000 | Tearney et al. | |
| 6,152,909 A | 11/2000 | Bagaoisan et al. | |
| 6,152,938 A | 11/2000 | Curry | |
| 6,156,046 A | 12/2000 | Passafaro et al. | |
| 6,157,852 A | 12/2000 | Selmon et al. | |
| 6,159,195 A | 12/2000 | Ha et al. | |
| 6,159,225 A | 12/2000 | Makower | |
| 6,165,127 A | 12/2000 | Crowley | |
| 6,179,859 B1 | 1/2001 | Bates et al. | |
| 6,183,432 B1 | 2/2001 | Milo | |
| 6,187,025 B1 | 2/2001 | Machek | |
| 6,190,353 B1 | 2/2001 | Makower et al. | |
| 6,191,862 B1 | 2/2001 | Swanson et al. | |
| 6,193,676 B1 | 2/2001 | Winston et al. | |
| 6,196,963 B1 | 3/2001 | Williams | |
| 6,206,898 B1 | 3/2001 | Honeycutt et al. | |
| 6,217,527 B1 | 4/2001 | Selmon et al. | |
| 6,217,549 B1 | 4/2001 | Selmon et al. | |
| 6,217,595 B1 | 4/2001 | Shturman et al. | |
| 6,221,049 B1 | 4/2001 | Selmon et al. | |
| 6,221,332 B1 | 4/2001 | Thumm et al. | |
| 6,228,049 B1 | 5/2001 | Schroeder et al. | |
| 6,228,076 B1 | 5/2001 | Winston et al. | |
| 6,231,546 B1 | 5/2001 | Milo et al. | |
| 6,231,549 B1 | 5/2001 | Noecker et al. | |
| 6,235,000 B1 | 5/2001 | Milo et al. | |
| 6,238,405 B1 | 5/2001 | Findlay, III et al. | |
| 6,241,667 B1 | 6/2001 | Vetter et al. | |
| 6,241,744 B1 | 6/2001 | Imran et al. | |
| 6,245,012 B1 | 6/2001 | Kleshinski | |
| 6,258,052 B1 | 7/2001 | Milo | |
| 6,263,236 B1 | 7/2001 | Kasinkas et al. | |
| 6,264,611 B1 | 7/2001 | Ishikawa et al. | |
| 6,266,550 B1 | 7/2001 | Selmon et al. | |
| 6,277,138 B1 | 8/2001 | Levinson et al. | |
| 6,283,951 B1 | 9/2001 | Flaherty et al. | |
| 6,283,983 B1 | 9/2001 | Makower et al. | |
| 6,299,622 B1 | 10/2001 | Snow et al. | |
| 6,299,623 B1 | 10/2001 | Wulfman | |
| 6,302,875 B1 | 10/2001 | Makower et al. | |
| 6,305,834 B1 | 10/2001 | Schubert et al. | |
| 6,312,444 B1 | 11/2001 | Barbut | |
| 6,319,242 B1 | 11/2001 | Patterson et al. | |
| 6,319,275 B1 | 11/2001 | Lashinski et al. | |
| 6,330,884 B1 | 12/2001 | Kim | |
| 6,355,005 B1 | 3/2002 | Powell et al. | |
| 6,361,545 B1 | 3/2002 | Macoviak et al. | |
| 6,375,615 B1 | 4/2002 | Flaherty et al. | |

(56) References Cited

U.S. PATENT DOCUMENTS

| | | | |
|---|---|---|---|
| 6,383,195 B1 | 5/2002 | Richard | |
| 6,383,205 B1 | 5/2002 | Samson et al. | |
| 6,394,976 B1 | 5/2002 | Winston et al. | |
| 6,398,798 B2 | 6/2002 | Selmon et al. | |
| 6,422,736 B1 | 7/2002 | Antonaides et al. | |
| 6,423,081 B1 | 7/2002 | Lee et al. | |
| 6,425,870 B1 | 7/2002 | Flesch | |
| 6,428,551 B1 | 8/2002 | Hall et al. | |
| 6,428,552 B1 | 8/2002 | Sparks | |
| 6,443,966 B1 | 9/2002 | Shiu | |
| 6,445,939 B1 | 9/2002 | Swanson et al. | |
| 6,447,525 B2 | 9/2002 | Follmer et al. | |
| 6,451,036 B1 | 9/2002 | Heitzmann et al. | |
| 6,454,779 B1 | 9/2002 | Taylor | |
| 6,475,226 B1 | 11/2002 | Belef et al. | |
| 6,482,217 B1 | 11/2002 | Pintor et al. | |
| 6,497,711 B1 | 12/2002 | Plaia et al. | |
| 6,501,551 B1 | 12/2002 | Tearney et al. | |
| 6,520,975 B2 | 2/2003 | Branco | |
| RE38,018 E | 3/2003 | Anctil et al. | |
| 6,532,380 B1 | 3/2003 | Close et al. | |
| 6,533,749 B1 | 3/2003 | Mitusina et al. | |
| 6,561,998 B1 | 5/2003 | Roth et al. | |
| 6,565,588 B1 | 5/2003 | Clement et al. | |
| 6,569,177 B1 | 5/2003 | Dillard et al. | |
| 6,592,526 B1 | 7/2003 | Lenker | |
| 6,620,180 B1 | 9/2003 | Bays et al. | |
| 6,623,437 B2 | 9/2003 | Hinchliffe et al. | |
| 6,623,495 B2 | 9/2003 | Findlay, III et al. | |
| 6,623,496 B2 | 9/2003 | Snow et al. | |
| 6,629,953 B1 | 10/2003 | Boyd | |
| 6,638,233 B2 | 10/2003 | Corvi et al. | |
| RE38,335 E | 11/2003 | Aust et al. | |
| 6,652,505 B1 | 11/2003 | Tsugita | |
| 6,652,548 B2 | 11/2003 | Evans et al. | |
| 6,656,195 B2 | 12/2003 | Peters et al. | |
| 6,666,874 B2 | 12/2003 | Heitzmann et al. | |
| 6,682,543 B2 | 1/2004 | Barbut et al. | |
| 6,733,511 B2 | 5/2004 | Hall et al. | |
| 6,740,103 B2 | 5/2004 | Werp et al. | |
| 6,746,462 B1 | 6/2004 | Selmon et al. | |
| 6,764,495 B2 | 7/2004 | Lee et al. | |
| 6,790,204 B2 | 9/2004 | Zadno-Azizi et al. | |
| 6,790,215 B2 | 9/2004 | Findlay, III et al. | |
| 6,818,001 B2 | 11/2004 | Wulfman et al. | |
| 6,830,577 B2 | 12/2004 | Nash et al. | |
| 6,843,797 B2 | 1/2005 | Nash et al. | |
| 6,849,068 B1 | 2/2005 | Bagaoisan et al. | |
| 6,863,676 B2 | 3/2005 | Lee et al. | |
| 6,911,026 B1 | 6/2005 | Hall et al. | |
| 6,919,057 B2 * | 7/2005 | Halstead | A61B 1/123 422/1 |
| 6,970,732 B2 | 11/2005 | Winston et al. | |
| 6,997,934 B2 | 2/2006 | Snow et al. | |
| 7,153,315 B2 | 12/2006 | Miller | |
| 7,172,610 B2 | 2/2007 | Heitzmann et al. | |
| 7,208,511 B2 | 4/2007 | Williams et al. | |
| 7,235,088 B2 | 6/2007 | Pintor et al. | |
| 7,318,831 B2 | 1/2008 | Alvarez et al. | |
| 7,388,495 B2 | 6/2008 | Fallin et al. | |
| 7,479,148 B2 | 1/2009 | Beaupre | |
| 7,488,322 B2 | 2/2009 | Brunnett et al. | |
| 7,524,289 B2 | 4/2009 | Lenker | |
| 7,603,166 B2 | 10/2009 | Casscells, III et al. | |
| 7,708,749 B2 | 5/2010 | Simpson et al. | |
| 7,713,235 B2 | 5/2010 | Torrance et al. | |
| 7,713,279 B2 | 5/2010 | Simpson et al. | |
| 7,729,745 B2 | 6/2010 | Maschke | |
| 7,734,332 B2 | 6/2010 | Sher | |
| 7,753,852 B2 | 7/2010 | Maschke | |
| 7,758,599 B2 | 7/2010 | Snow et al. | |
| 7,771,444 B2 | 8/2010 | Patel et al. | |
| 7,887,556 B2 | 2/2011 | Simpson et al. | |
| 8,226,675 B2 | 7/2012 | Simpson et al. | |
| 8,245,845 B1 * | 8/2012 | Huddleston | A61B 90/70 15/218.1 |
| 8,431,076 B2 * | 4/2013 | Fraundorfer | A61L 2/183 134/25.1 |
| 2001/0000041 A1 | 3/2001 | Selmon et al. | |
| 2001/0031784 A1 | 10/2001 | Petersen et al. | |
| 2001/0031981 A1 | 10/2001 | Evans et al. | |
| 2001/0044622 A1 | 11/2001 | Vardi et al. | |
| 2001/0049500 A1 | 12/2001 | Van Tassel et al. | |
| 2002/0019644 A1 | 2/2002 | Hastings et al. | |
| 2002/0022788 A1 | 2/2002 | Corvi et al. | |
| 2002/0058904 A1 | 5/2002 | Boock et al. | |
| 2002/0077373 A1 | 6/2002 | Hudson | |
| 2002/0077642 A1 | 6/2002 | Patel et al. | |
| 2002/0095141 A1 | 6/2002 | Belef et al. | |
| 2002/0103459 A1 | 8/2002 | Sparks et al. | |
| 2002/0177800 A1 | 11/2002 | Bagaoisan et al. | |
| 2002/0188307 A1 | 12/2002 | Pintor et al. | |
| 2003/0018346 A1 | 1/2003 | Follmer et al. | |
| 2003/0023263 A1 | 1/2003 | Krolik et al. | |
| 2003/0093098 A1 | 5/2003 | Heitzmann et al. | |
| 2003/0120295 A1 | 6/2003 | Simpson et al. | |
| 2003/0125757 A1 | 7/2003 | Patel et al. | |
| 2003/0125758 A1 | 7/2003 | Simpson et al. | |
| 2003/0163126 A1 | 8/2003 | West, Jr. | |
| 2003/0199747 A1 | 10/2003 | Michlitsch et al. | |
| 2003/0206484 A1 | 11/2003 | Childers et al. | |
| 2003/0229369 A1 | 12/2003 | Findlay, III et al. | |
| 2004/0006358 A1 | 1/2004 | Wulfman et al. | |
| 2004/0049225 A1 | 3/2004 | Denison | |
| 2004/0118440 A1 * | 6/2004 | Sasaki | A61B 90/70 134/166 C |
| 2004/0167553 A1 | 8/2004 | Simpson et al. | |
| 2004/0167554 A1 | 8/2004 | Simpson et al. | |
| 2004/0193034 A1 | 9/2004 | Wasicek et al. | |
| 2004/0210245 A1 | 10/2004 | Erickson et al. | |
| 2005/0004585 A1 | 1/2005 | Hall et al. | |
| 2005/0004594 A1 | 1/2005 | Nool et al. | |
| 2005/0021063 A1 | 1/2005 | Hall et al. | |
| 2005/0042239 A1 | 2/2005 | Lipiecki et al. | |
| 2005/0090845 A1 | 4/2005 | Boyd | |
| 2005/0090849 A1 | 4/2005 | Adams | |
| 2005/0177068 A1 | 8/2005 | Simpson | |
| 2005/0191222 A1 * | 9/2005 | Lin | A61L 2/14 422/300 |
| 2005/0216018 A1 | 9/2005 | Sennett | |
| 2005/0222596 A1 | 10/2005 | Maschke | |
| 2005/0222663 A1 | 10/2005 | Simpson et al. | |
| 2006/0015126 A1 | 1/2006 | Sher | |
| 2006/0235334 A1 | 10/2006 | Corvi et al. | |
| 2006/0259052 A1 | 11/2006 | Pintor et al. | |
| 2007/0010840 A1 | 1/2007 | Rosenthal et al. | |
| 2007/0038061 A1 | 2/2007 | Huennekens et al. | |
| 2007/0049958 A1 | 3/2007 | Adams | |
| 2007/0135712 A1 | 6/2007 | Maschke | |
| 2007/0135886 A1 | 6/2007 | Maschke | |
| 2007/0142785 A1 * | 6/2007 | Lundgaard | A61M 5/1418 604/179 |
| 2007/0167824 A1 | 7/2007 | Lee et al. | |
| 2007/0215190 A1 | 9/2007 | Efinger et al. | |
| 2007/0225739 A1 | 9/2007 | Pintor et al. | |
| 2007/0265647 A1 | 11/2007 | Bonnette et al. | |
| 2007/0276419 A1 | 11/2007 | Rosenthal | |
| 2008/0001643 A1 | 1/2008 | Lee | |
| 2008/0004644 A1 | 1/2008 | To et al. | |
| 2008/0004645 A1 | 1/2008 | To et al. | |
| 2008/0004646 A1 | 1/2008 | To et al. | |
| 2008/0004647 A1 | 1/2008 | To et al. | |
| 2008/0045986 A1 | 2/2008 | To et al. | |
| 2008/0051812 A1 | 2/2008 | Schmitz et al. | |
| 2008/0065124 A1 | 3/2008 | Olson | |
| 2008/0065125 A1 | 3/2008 | Olson | |
| 2008/0097403 A1 | 4/2008 | Donaldson et al. | |
| 2008/0125799 A1 | 5/2008 | Adams | |
| 2008/0161840 A1 | 7/2008 | Osiroff et al. | |
| 2008/0177139 A1 | 7/2008 | Courtney et al. | |
| 2008/0208227 A1 | 8/2008 | Kadykowski et al. | |
| 2008/0249553 A1 | 10/2008 | Gruber et al. | |
| 2008/0312673 A1 | 12/2008 | Viswanathan et al. | |

(56) References Cited

U.S. PATENT DOCUMENTS

| | | | |
|---|---|---|---|
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2012/0330336 A1 | 12/2012 | Simpson et al. |
| 2014/0166054 A1* | 6/2014 | Moberg ............. A61B 90/70 134/22.12 |
| 2014/0190523 A1* | 7/2014 | Garvey ............. A61B 90/70 134/22.12 |
| 2015/0342694 A1* | 12/2015 | Morejon ............. A61M 25/00 134/22.11 |
| 2015/0374401 A1* | 12/2015 | Guggenheimer .... A61B 17/221 604/256 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 9316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

International Search Report and Written Opinion for Application No. PCT/US2015/037800, dated Sep. 10, 2015, 10 pages, Rijswijk, NL.

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

* cited by examiner

US 10,314,667 B2

CLEANING DEVICE FOR CLEANING MEDICAL INSTRUMENT

CROSS-REFERENCE TO RELATED APPLICATION

The present application claims the benefit of U.S. Provisional Application Ser. No. 62/137,887, filed Mar. 25, 2015, the entirety of which is hereby incorporated by reference.

FIELD OF THE DISCLOSURE

Aspects of the present invention generally relate to a cleaning device for cleaning a medical instrument.

BACKGROUND OF THE DISCLOSURE

Certain medical instruments such as tissue removal catheters require cleaning to remove collected debris. For example, some tissue removal catheters include a tissue collection chamber that collects excised tissue and other debris that is cut away or otherwise extracted from a vascular or other biological lumen. When tissue collection chambers become full they can be cleaned to empty the collected tissue.

SUMMARY OF THE DISCLOSURE

In one aspect, a cleaning device for cleaning a medical instrument, such as a tissue-removal catheter, defines a flushing chamber and includes first and second sealing members. The cleaning device receives a medical instrument between the first and second sealing members so that the medical instrument extends through the flushing chamber. When the cleaning device is closed, the sealing members engage one another to seal the flushing chamber and engage the medical instrument to form a seal thereabout. Portions of at least one of the sealing members are disposed within the flushing chamber. Positive pressure in the flushing chamber urges portions of the sealing members disposed within the flushing chamber in a direction that enhances the tightness of the seal interface between the sealing members. Likewise, positive pressure urges portions of the sealing members disposed within the flushing chamber toward the medical instrument to enhance the tightness of the seal interface formed with the medical instrument. Fluid in the flushing chamber flows into an opening in the medical instrument disposed within the flushing chamber, through an instrument lumen, and out another opening disposed outside the flushing chamber, thereby flushing debris from the instrument lumen.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
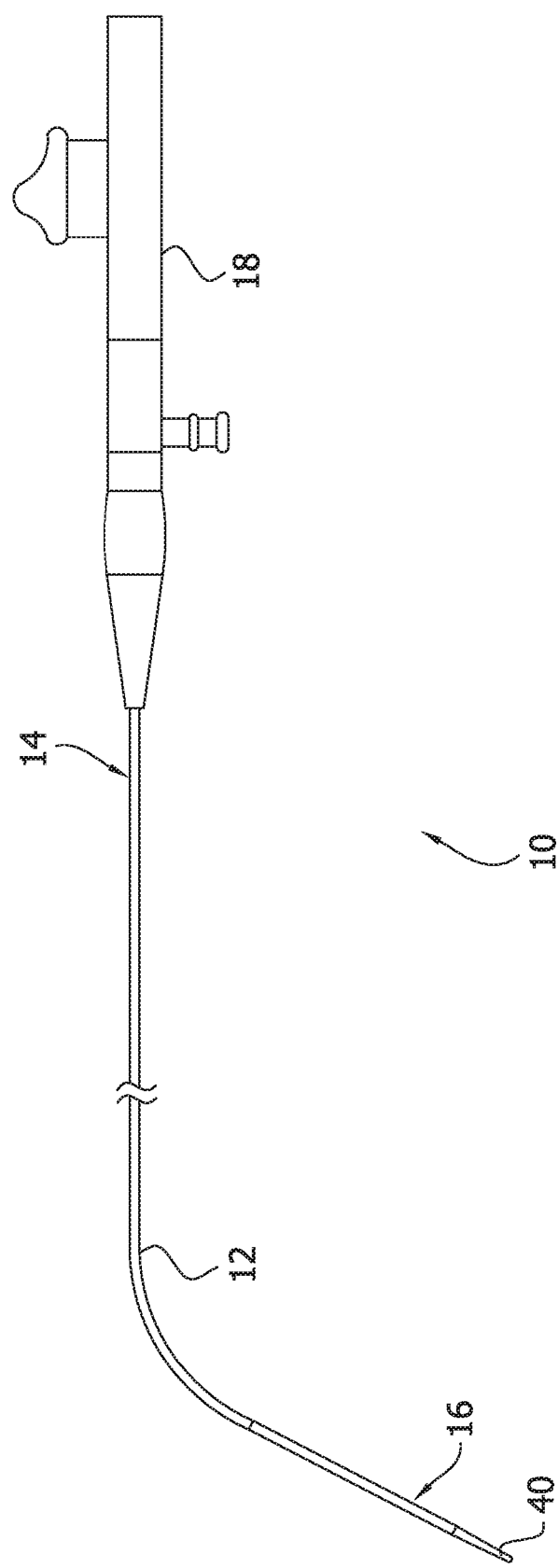
FIG. 1 is a schematic of a catheter suitable for cleaning with a cleaning device.

Referring to FIG. 1, a catheter is generally indicated at reference number 10. The catheter 10 includes an elongate catheter body, generally indicated at reference numeral 12, that is sized to be inserted in a biological lumen to extract and remove tissue and/or other luminal debris. For example, the catheter body 12 can track along guide wire (not shown) that extends through a biological lumen to be inserted therein. Examples of biological lumens include, but are not limited to, an artery, vein, duct, etc. The catheter body 12 has a proximal end portion, generally indicated at 14, and a distal end portion, generally indicated at 16. A handle adaptor 18 is attached to the proximal end portion 14 of the body 12. In the illustrated embodiment the handle adaptor 18 is configured to be received in a handle (not shown). In the illustrated embodiment, the handle and handle adaptor 18 include various features that can be used to control operation of the catheter 10 in use. The illustrated catheter 10 is an atherectomy catheter, though it is contemplated that other types of catheters can also be used without departing from the scope of the invention.

Figure 2A:
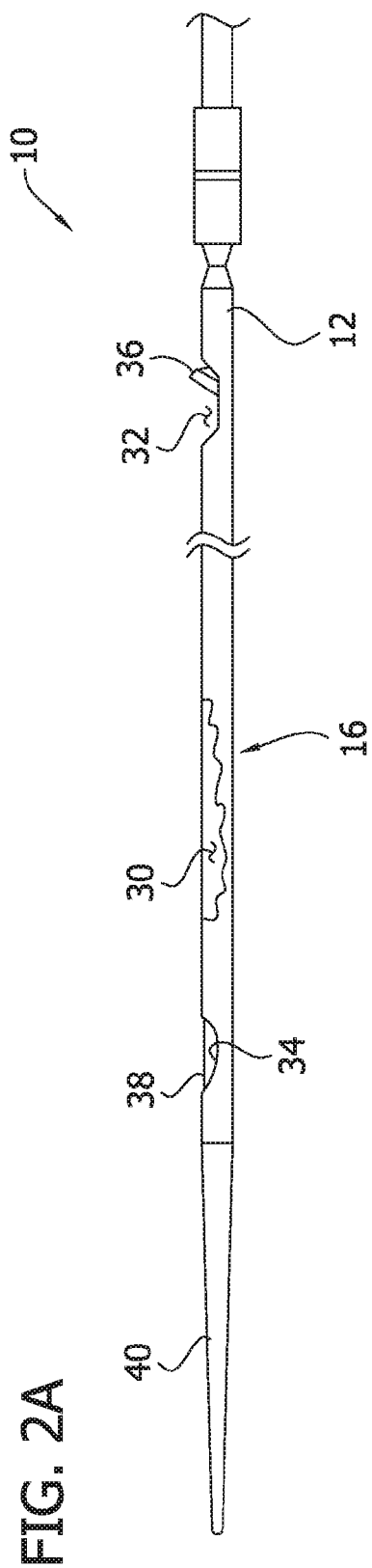
FIG. 2A is an enlarged view of a distal end portion of the catheter having a portion thereof broken away to reveal a catheter lumen, a distal opening of the catheter lumen being in a closed configuration.

As shown in FIG. 2A, the distal end portion 16 of the catheter body 12 defines a catheter lumen 30 that extends from a proximal opening 32 to a distal opening 34. The catheter lumen 30 is in fluid communication with the proximal opening 32 and the distal opening 34. The distal end portion 16 of the catheter body 12 can also have one or more openings (e.g., micron-sized openings, not shown) between the proximal and distal openings 32, 34 that are in fluid communication with the catheter lumen 30 and are sized to allow fluid (e.g., blood) to flow therethrough but not removed tissue. In the illustrated embodiment, the proximal opening 32 is a cutter window. In a deployed position (FIG. 2A), the cutting element 36 is configured to extend through the cutter window 32 and engage tissue on the wall of the biological lumen. In the deployed position, the cutting element 36 is configured to rotate at a relatively high speed to slice through tissue in the biological lumen. The catheter body 12 is configured to slide through the biological lumen in the distal direction as the cutting element 36 rotates. The catheter 10 is configured such that rotational motion of the cutting element 36 and the translational motion of the catheter body 12 direct cut tissue in the distal direction into the catheter lumen 30. Thus, in the illustrated embodiment, the catheter lumen 30 functions as a tissue collection chamber. In a stored position (FIG. 2B), the cutting element 36 is movable relative to the catheter body 12 so it can be drawn into the cutter window 32.

Figure 2B:
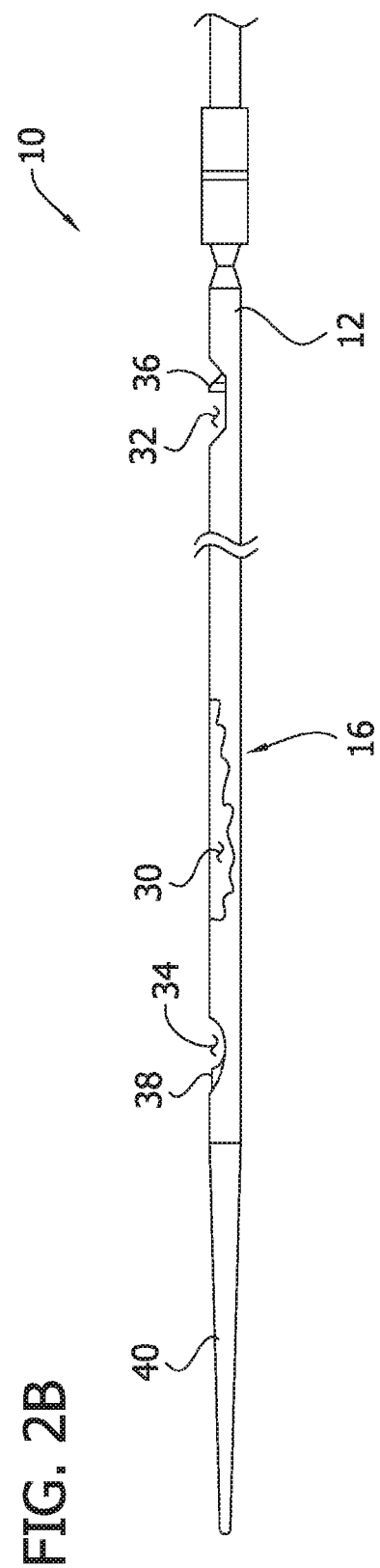
FIG. 2B is similar to FIG. 2A with the distal opening in an open configuration.

In FIG. 2A, the distal opening 34 of the distal end portion 16 is closed by a closure member 38. In this configuration, the closure member 38 is positioned to prevent cut tissue from escaping the tissue collection chamber 30 through the distal opening 34. As shown in FIG. 2B, the closure member 38 is configured to be rotated about its axis to open the distal opening 34 so that the tissue contained in the tissue collection chamber 30 can be flushed out through the distal opening after removing the catheter 10 from the biological lumen. In the illustrated embodiment, a distal tip 40 of the catheter 10 is rotatably secured to the catheter body 12 and fixedly connected to the closure member 38. To open the distal opening 34, the distal tip 40 of the catheter 10 is rotated relative the catheter body 12, thereby imparting rotation to the closure member 38 relative to the catheter body and opening the distal opening.

Figure 3:
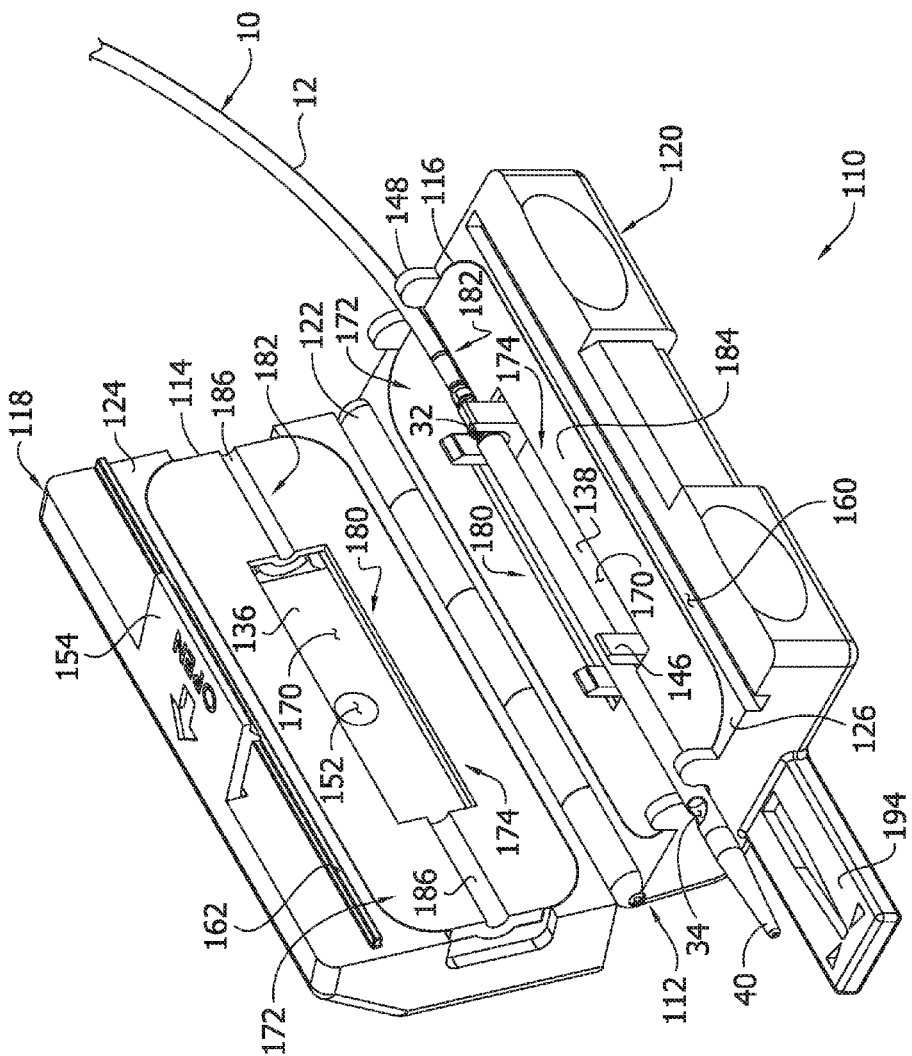
FIG. 3 is a perspective of the cleaning device and the catheter, the cleaning device being in an open configuration.

Referring to FIG. 3, a cleaning device for cleaning a medical instrument, such as the catheter 10 or another suitable catheter, is generally indicated at reference number 110. The cleaning device 110 is configured to remove tissue and/or debris contained in the catheter lumen 30 of the catheter 10 by directing flushing fluid into the proximal opening 32, through the catheter lumen, and out the distal opening 34. Fluid delivered under pressure can be used to flush tissue and debris from the catheter lumen 30 without leaking through the cleaning device 110. As discussed in greater detail below, the device 110 is configured and arranged so that the tightness of seal interfaces that prevent fluid from leaking from the device is enhanced as the fluid pressure used to flush out the catheter lumen 30 increases. It will be understood that the cleaning device 110 can be configured to clean other types of medical instruments other than the catheter 10 without departing from the scope of the invention. Preferably, other medical instruments that can be cleaned with the cleaning device 110 each include an instrument lumen (e.g., in the illustrated embodiment, the tissue collection chamber 30), a fluid inlet (e.g., in the illustrated embodiment, the proximal opening 32) in fluid communication with the instrument lumen and a fluid outlet (e.g., in the illustrated embodiment, the distal opening 34) in fluid communication with the instrument lumen.

Figure 5:
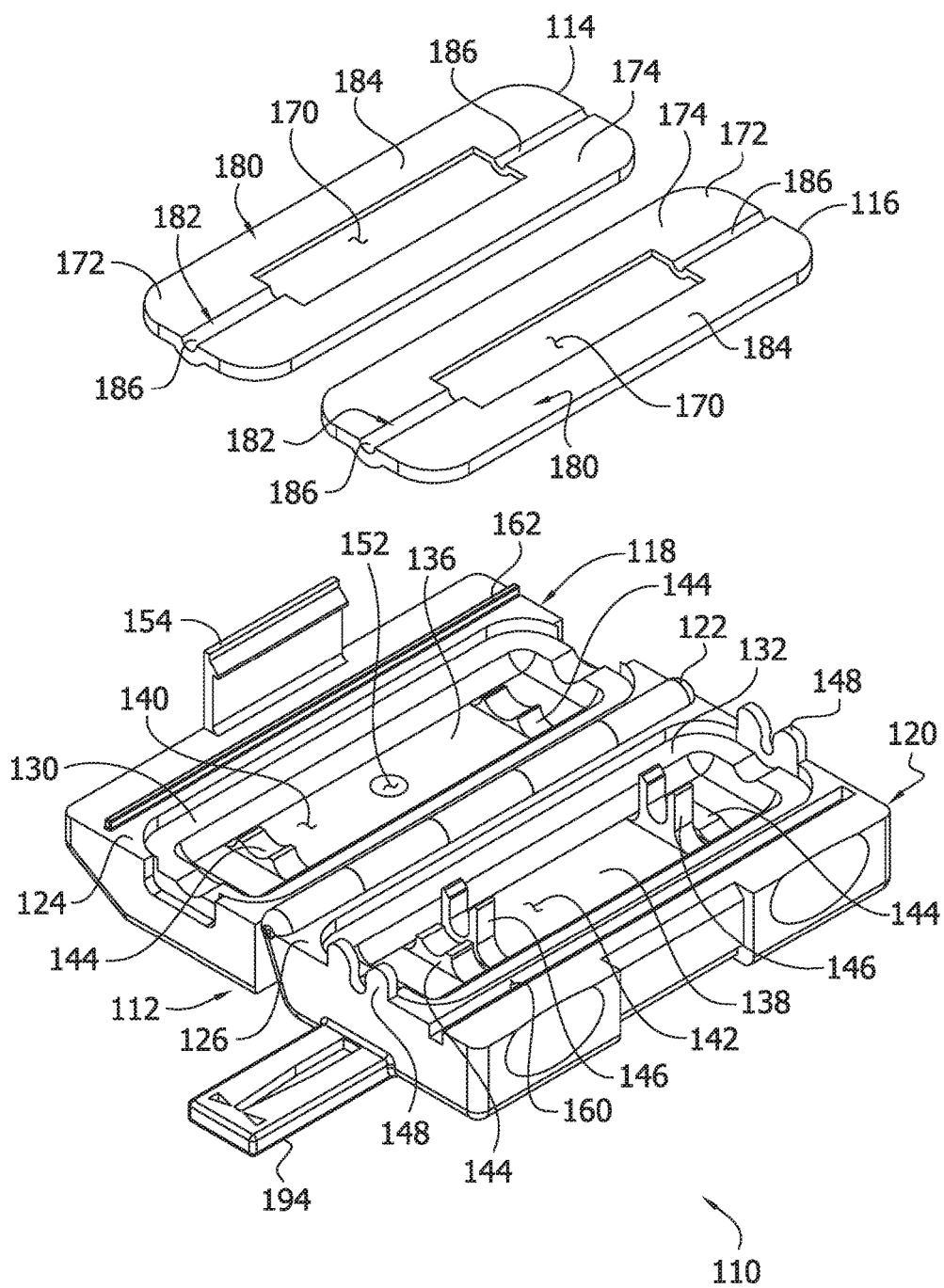
FIG. 5 is an exploded perspective of the cleaning device.

Referring to FIG. 5, the cleaning device 110 comprises a device body, generally indicated at 112, and upper and lower sealing members, generally indicated at 114, 116, respectively (broadly, first and second sealing members) secured to the device body. In particular, the device body 112 includes upper and lower body portions, generally indicated at 118, 120, respectively (broadly, first and second body portions), to which the upper and lower sealing members 114, 116 are respectively secured. As used throughout the present disclosure with respect to the cleaning device 110 and components thereof, the terms defining relative locations and positions of structures and components thereof, including but not limited to the terms "upper," "lower," "right," "left," "top," and "bottom," are meant to provide a point of reference for such components and structures as shown in the drawings, with the understanding that the respective relative locations of such components and structures will depend on the orientation of the channel framing and joiner in use. In the illustrated embodiment, the upper and lower body portions 118, 120 are separately formed, plastic injection molded pieces. However, in other embodiments, it is contemplated that a device body can be made from different materials and formed in different ways without departing from the scope of the invention. The upper and lower body portions 118, 120 can be made from opaque materials or transparent materials to enable viewing of internal aspects of the cleaning device 110 in use.

Figure 4:
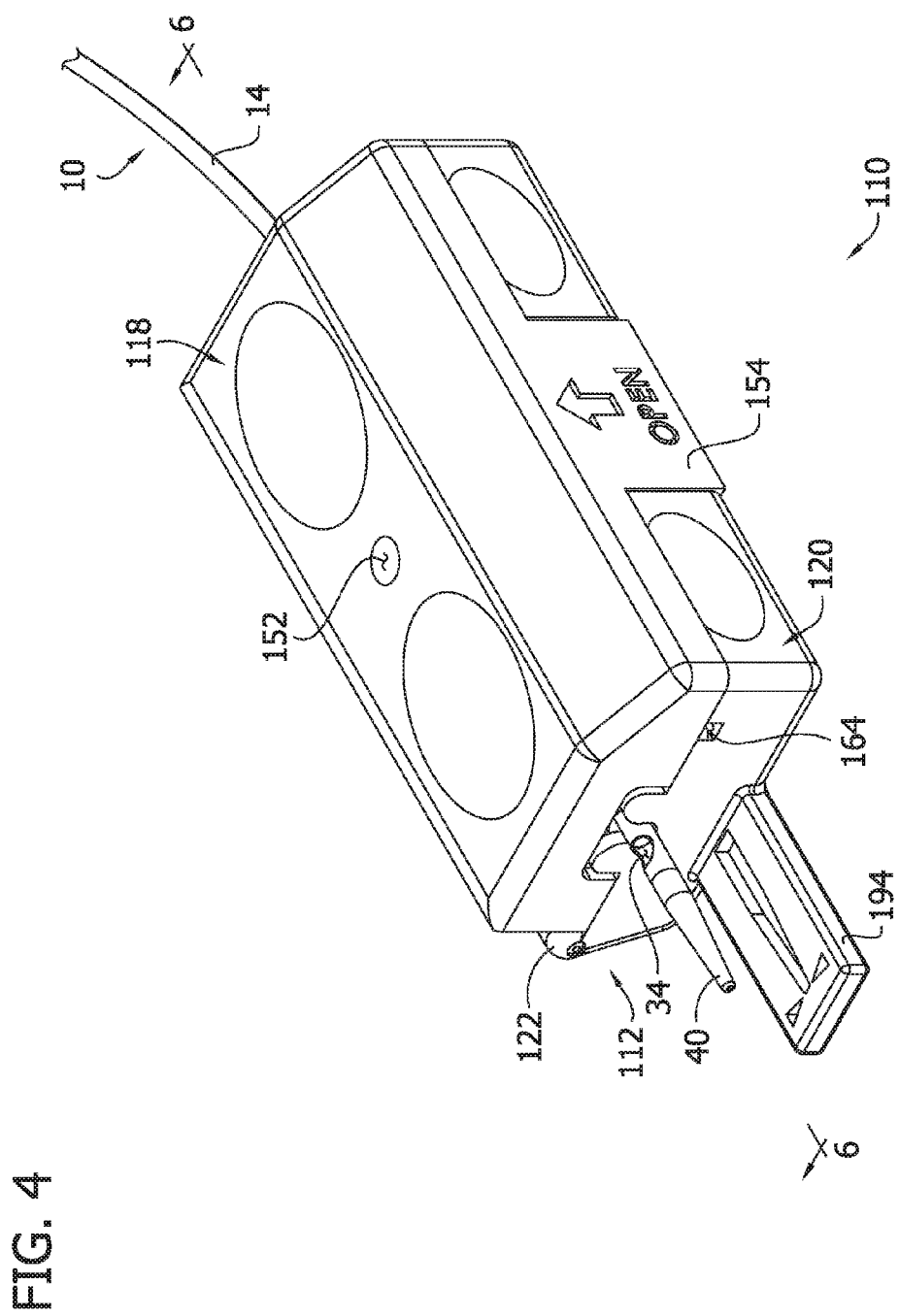
FIG. 4 is similar to FIG. 3 with the cleaning device being in a closed configuration.

The upper and lower body portions 118, 120 are hingedly connected to one another by a piano hinge, generally indicated at 122. The upper and lower body portions 118, 120 are configured to pivot relative to one another about a hinge axis of the piano hinge to configure the device 110 between an open position (FIG. 3) and a closed position (FIG. 4). It is understood that the upper and lower body portions 118, 120 may be connected in other ways and/or may be configured to be completely disconnected in the open position, without departing from the scope of the invention. In general, the device 110 is configured to receive the catheter 10 between the upper and lower body portions 118, 120 and the upper and lower sealing members 114, 116 when the device is open. Moreover, the device 110 is configured to receive the catheter 10 between the upper and lower body portions 118, 120 while the catheter body 12 is received on a guide wire so that the catheter lumen 30 can be cleaned without removing the catheter from the guide wire.

As shown in FIG. 5, the upper and lower body portions 118, 120 have respective inner faces 124, 126. When the device 110 is closed, the inner faces 124, 126 are generally abutting and in opposing relationship with respect to one another. When the device 110 is open, the inner faces 124, 126 are spaced apart for receiving the catheter 10 therebetween. The inner faces 124, 126 of the upper and lower body portions 118, 120 define recessed seal seats 130, 132. As discussed in further detail below, the recessed seats 130, 132 are sized to receive the upper and lower sealing members 114, 116 so that the laterally outer portions of the inner faces 124, 126 are substantially flush with the inner surfaces of the sealing members received therein. The inner face 124 of the upper body portion 118 also defines a recessed upper chamber surface 136 defining an upper cavity 140, and the inner face 126 of the lower body portion 120 also defines a recessed lower chamber surface 138 defining a lower cavity 142.

The upper and lower body portions 118, 120 include seal supports 144 (e.g., two seal supports for each body portion) extending downward and upward, respectively, from the respective chamber surfaces 136, 138 adjacent opposite ends of the device body to support portions of the sealing members 114, 116. The lower body portion 120 includes two loose fit guides 146, which project upward from the lower chamber surface 138. As shown in FIG. 3, the loose fit guides 146 are configured to loosely engage the catheter 10 received between the upper and lower body portions 118, 120 to position the catheter in a proper position relative opposite sides of the device body 112. In addition, the lower body portion 120 includes snap-fit guides 148 configured to engage the catheter 10 received between the upper and lower body portions 118, 120 to secure the catheter to the lower body portion when the device body 112 is in the open position.

Figure 6:
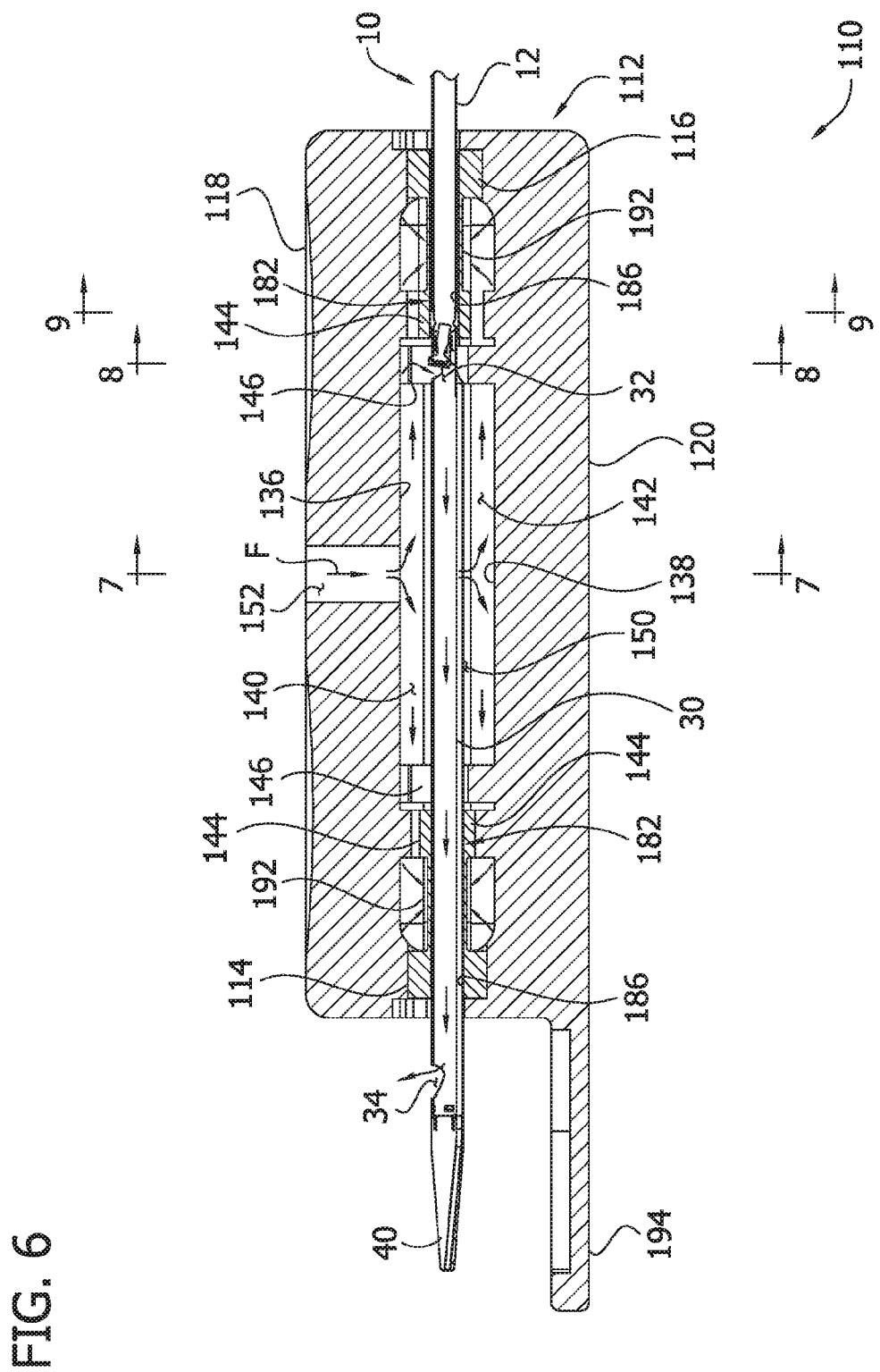
FIG. 6 is sectional view taken along the line 6-6 of FIG. 4.
Figure 7:
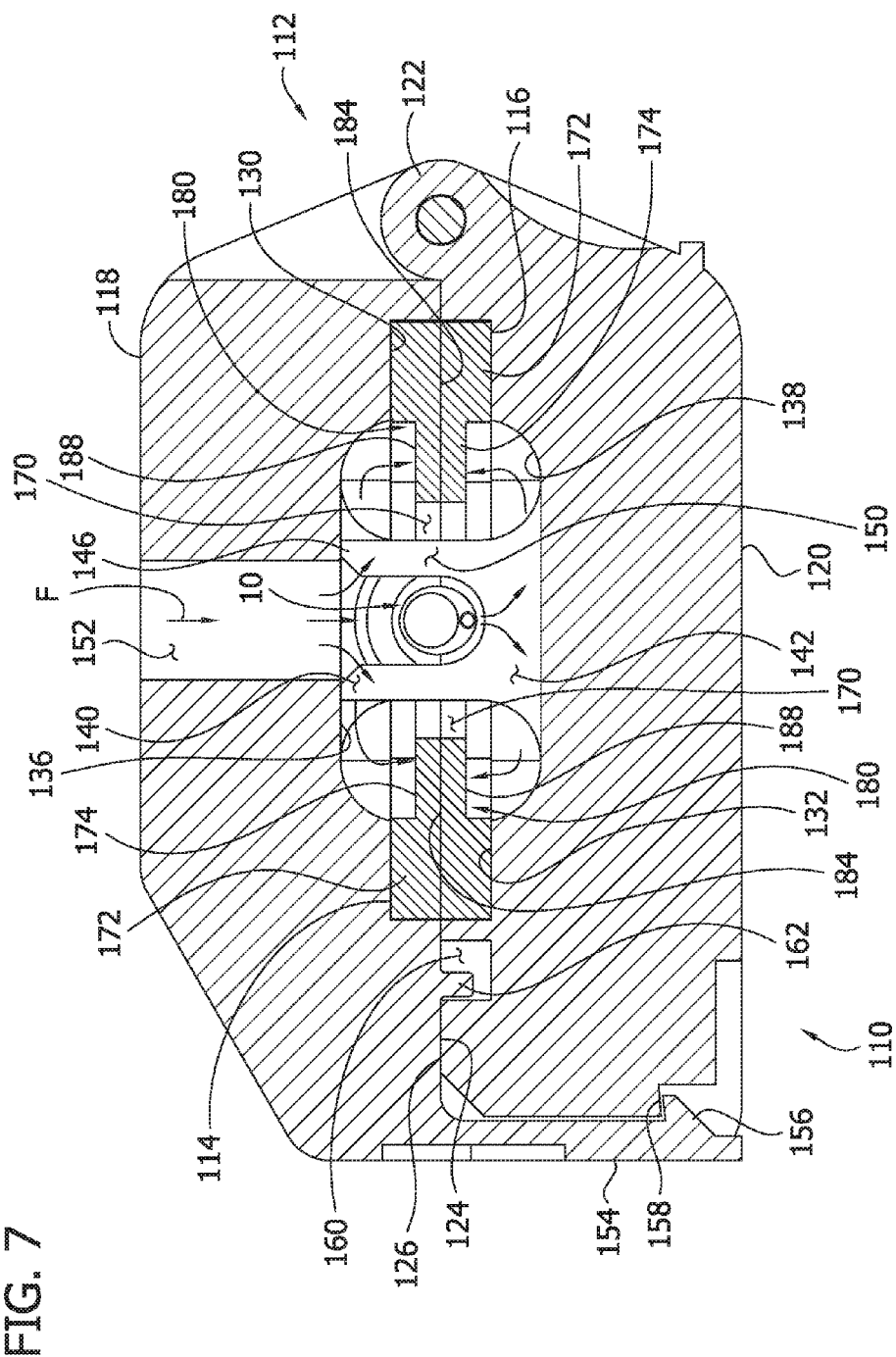
FIG. 7 is a sectional view taken along the line 7-7 of FIG. 6.

As shown in FIGS. 6 and 7, when the device body 112 is in the closed position, the upper and lower cavities 140, 142 define an internal flushing chamber 150 in the device body. The upper body portion 118 has an inlet port 152 that extends through the device body 112 and opens toward the upper cavity 140 in fluid communication with the internal flushing chamber 150. In use, the inlet port 152 is configured to fluidly connect a source of flushing fluid (not shown) to the internal flushing chamber 150. As shown in FIG. 5, the cavities 140, 142 each have an inner perimeter edge at the junctions of the chamber surfaces 136, 138 and the recessed seal seats 130, 132. When the device body 112 is in the closed position as shown in FIGS. 6 and 7, the inner perimeter edges of the cavities 140, 142 substantially align.

As will be discussed in greater detail below, the flushing chamber 150 is configured to receive and contain a flushing fluid up to a maximum positive pressure (i.e., a maximum pressure greater than atmospheric pressure). As shown in FIG. 7, a clip 154 secures the upper body portion 118 to the lower body portion 120 to prevent the device body 112 from opening when the flushing chamber 150 contains a fluid at or below the maximum positive pressure. The clip 154 has a latching portion 156 configured to interlock with a latch-receiving structure 158 of the lower body portion 116. When the latching portion 156 of the clip 154 interlocks with the latch receiving structure 158 of the lower body portion 120, the clip secures the device body 112 in the closed position. The interlocking engagement between the clip 154 and the lower body portion 120 prevents the upper and lower body portions 118, 120 from separating when the internal flushing chamber 150 contains a pressurized fluid. Although the illustrated cleaning device 110 uses the clip 154 to secure the device body 112 in the closed position, it will be understood that other securement mechanisms can be used without departing from the scope of the invention.

Referring to FIGS. 3 and 7, the lower body portion 120 includes a gutter 160 and the upper body portion 118 includes a baffle 162. As shown in FIG. 7, when the cleaning device 110 is closed, the baffle 162 projects downward into the gutter 160. As will be discussed in greater detail below, the sealing members 114, 116 are configured to seal the internal flushing chamber 150 during use so that flushing fluid directed into the flushing chamber 150 through the inlet port 152 does not leak between the inner faces 124, 126 of the upper and lower body portions 118, 120. If, however, fluid leaks between the seal interface of the sealing members 114, 116 during use, the baffle 162 directs the leaking fluid into the gutter 160 to control the discharge of fluid from the flushing chamber 150. As shown in FIG. 4, the gutter 160 has a discharge port 164. Leaked fluid is directed through the gutter 160 and out the discharge port 164 in a controlled manner. The gutter 160 and baffle 162 may be omitted and other ways of controlling the discharge of leaking fluid from a flushing chamber can also be used without departing from the scope of the invention.

Figure 9:
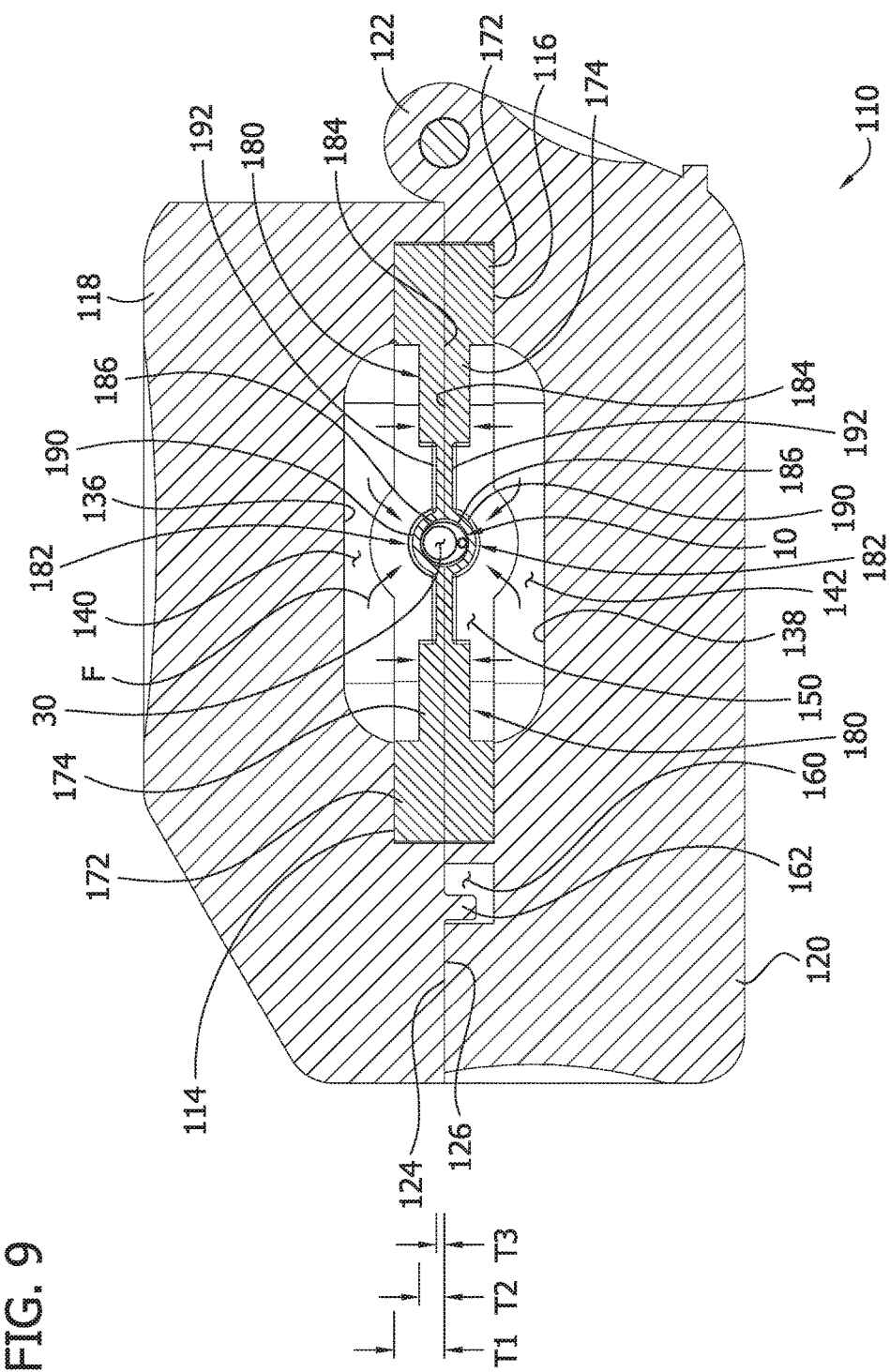
FIG. 9 is a sectional view taken along the line 9-9 of FIG. 6.

Referring to FIG. 5, the sealing members 114, 116 are generally rectangular panels of compressively resilient material that each has an inner perimeter defining a seal opening 170. As shown in FIG. 3, when the lower sealing member 116 is received in the recessed seal seat 132, the loose fit catheter guides 146 extend up through the seal opening 170 thereof. Likewise, as shown in FIG. 7, when the cleaning device 110 is closed, the loose fit catheter guides 146 extend through the seal openings 170 in both of the sealing members 114, 116. The sealing members 114, 116 are received in and secured to (e.g., using adhesives or interlocking features) the recessed seal seats 130, 132 of the upper and lower body portions 118, 120. In particular, as shown in FIG. 7, outer border portions 172 of the sealing members 114, 116 engage and are secured to the respective seal seats 130, 132. Inner portions 174 of the sealing members 114, 116 extend inward past the inner perimeter edges of the respective cavities 140, 142 and into the flushing chamber 150 so that the inner portion of each sealing member 114, 116 extends over a respective chamber surface 136, 138. The inner portions 174 have inner peripheries defining the seal openings 170. In the illustrated embodiment, a thickness T1 of the outer border portion 172 of each of the sealing members 114, 116 is greater than a thickness T2 of the inner portion 174 (FIG. 9).

The sealing members 114, 116 are configured to engage one another and the catheter 10 to seal the flushing chamber 150 when the device 110 is closed. As shown in FIG. 5, each of the sealing members 114, 116 has a chamber sealing portion, generally indicated at 180, for sealingly engaging the chamber sealing portion of the other of the sealing members. Each of the sealing members 114, 116 also includes a pair of catheter sealing portions, generally indicated at 182, for sealingly engaging the catheter 10 extending through the cleaning device 110 in the closed position. The engagement between the chamber sealing portions 180 of the upper and lower sealing members 114, 116, in combination with the engagement between the catheter sealing portions 182 of the sealing members and the catheter 10, preferably provides a liquid or fluid tight seal of the flushing chamber 150 so that pressurized fluid (e.g., liquid) in the flushing chamber does not leak through the seal interfaces.

Referring to FIG. 7, the chamber sealing portion 180 of each of the sealing members 114, 116 includes a flat engagement surface 184 (e.g., an inner surface) configured to sealingly engage the opposing flat engagement surface of the other sealing member. The flat engagement surface 184 of the chamber sealing portion 180 of each of the sealing members 114, 116 forms a substantially continuous surface with the outer portions of the inner face 124, 126 of the respective device body portion 118, 120. As a result, when the device 110 is closed, as shown in FIG. 7, and outer portions of the inner faces 124, 126 of the upper and lower body portions 118, 120 oppose and engage one another in substantial alignment, the flat engagement surfaces 184 of the upper and lower sealing members 114, 116 likewise oppose and engage one another in substantial alignment. Though the illustrated engagement surfaces 184 are substantially flush with the outer portions of the inner faces 124, 126, it is contemplated that engagement surfaces could be raised relative the inner faces of the body portions without departing from the scope of the invention. In that case, the sealing members could be held together in compression (e.g., by the clip 154) when the device is closed, which would enhance the tightness of the seal interface between the sealing members.

Figure 10:
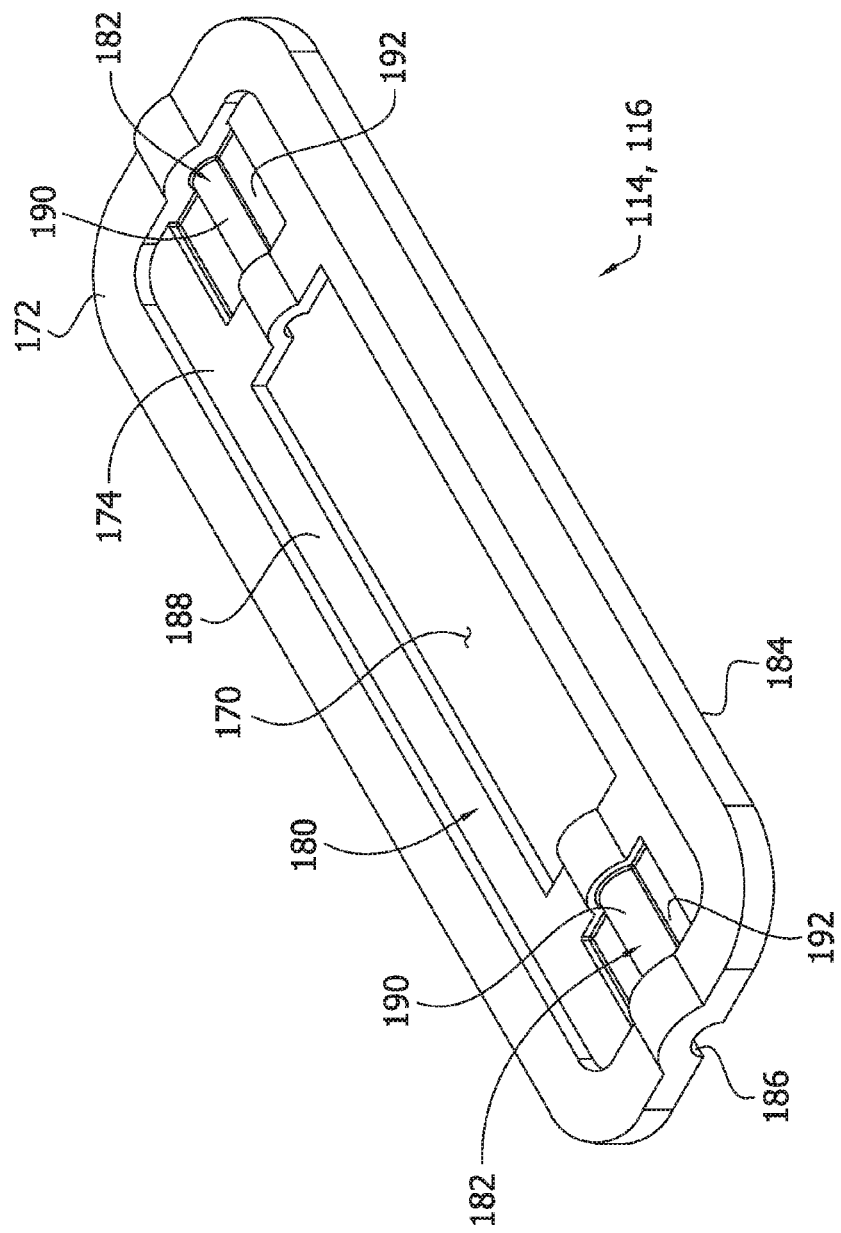
FIG. 10 is a perspective of a sealing member of the cleaning device.

Referring to FIG. 7, when the cleaning device 110 is closed, the chamber sealing portions 180 of the upper and lower sealing members 114, 116 (more specifically, the inner portions 174 thereof) extend into the flushing chamber 150 around substantially the entirety of the respective interior perimeter edges of the recessed upper and lower chamber surfaces 136, 138. The flat engagement surfaces 184 of the chamber sealing portions 180 engage one another within the flushing chamber 150 to form a seal interface therein. Within the flushing chamber 150, the chamber sealing portions 180 of each the sealing members 114, 116 (more specifically, the inner portions 174 thereof) have pressure surfaces 188 (see also FIG. 10) opposite the flat engagement surfaces 184. As shown in FIG. 7, each of the pressure surfaces 188 faces (i.e., opposes) a respective one of the recessed chamber surfaces 136, 138 and is spaced apart from it.

Figure 8:
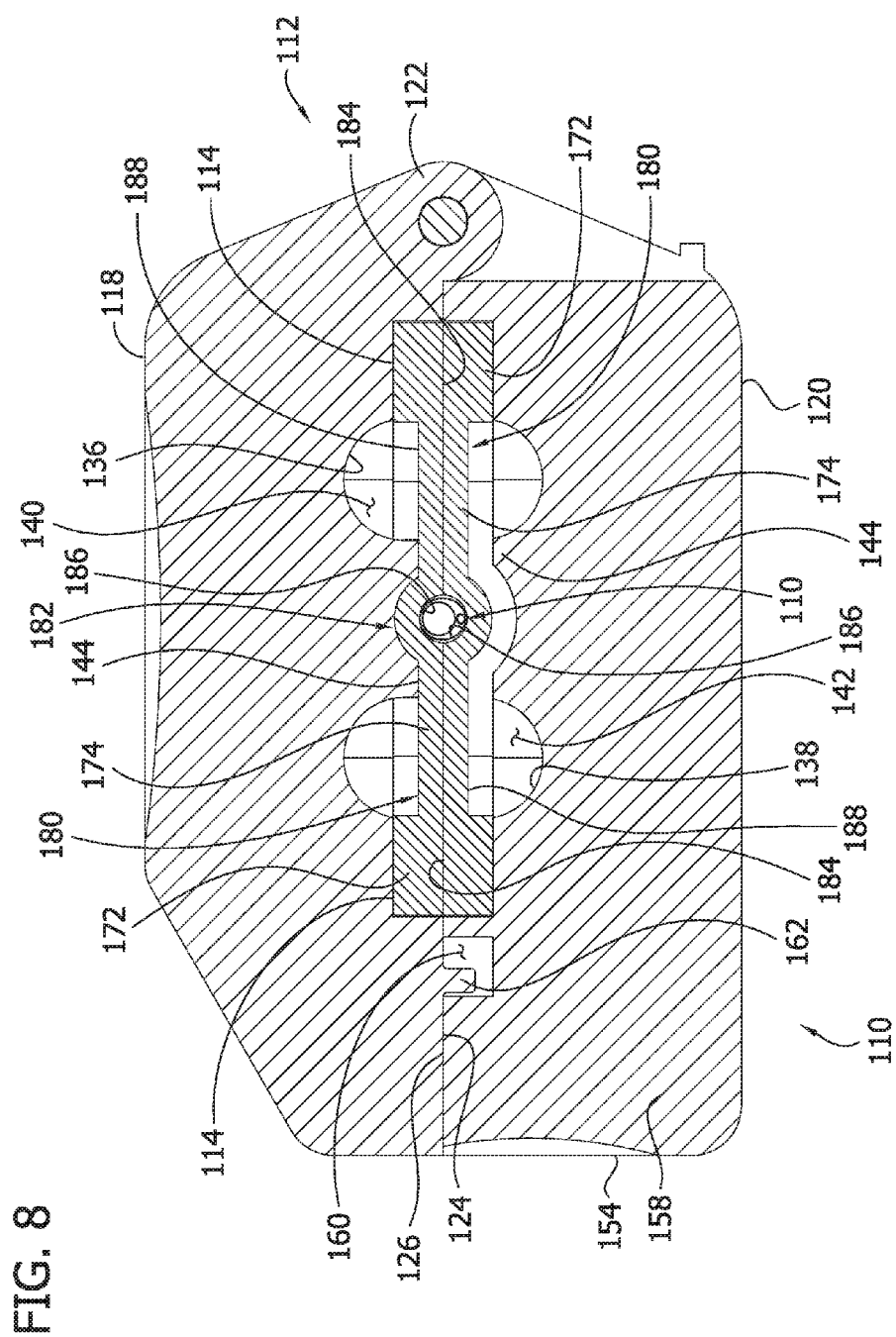
FIG. 8 is a sectional view taken along the line 8-8 of FIG. 6.

As shown in FIG. 5, each of the catheter sealing portions 182 of the sealing members 114, 116 includes a groove defining an axially extending concave surface 186 sized for sealing engagement with a portion of the catheter 10. As shown in FIGS. 8 and 9, when the catheter 10 extends through the cleaning device 110 in the closed position, the concave surfaces 186 of the upper sealing member 114 engage upper portions of the catheter 10, and the concave surfaces of the lower sealing member 116 engage lower portions of the catheter. Preferably the concave surfaces 186 of the upper and lower sealing members 114, 116 sealingly engage the catheter 10 around the entire circumference of the catheter 12 at two axially spaced apart locations (e.g., proximal and distal locations) adjacent the longitudinal ends of the flushing chamber 150.

As shown in FIGS. 8 and 9, the catheter sealing portions 182 of the upper and lower sealing members 114, 116 also extend into the flushing chamber 150 adjacent the longitudinal ends of the chamber. The concave surfaces 186 of the catheter sealing portions 182 engage the catheter 10 at axially spaced apart locations along the catheter within the flushing chamber. The seal support members 144 support the catheter sealing portions 182 in an operative position within the flushing cavity 150 (i.e., a position at which the concave surfaces 186 sealingly engage the catheter 10 when the cleaning device 110 is closed). As shown in FIG. 9, the catheter sealing portions 182 of each of the sealing members 114, 116 have outwardly facing pressure surfaces 190 opposite the concave sealing surfaces 186. Each of the pressure surfaces 190 of the catheter sealing portions 182 faces (i.e., opposes) a respective one of the recessed chamber surfaces 136, 138 and is spaced apart from it. Each of the catheter sealing portions 182 and adjacent areas of the chamber sealing portions 180 have thinned regions 192 with a thickness T3 that is less than the thickness T2 of the remaining interior portions 174 of the chamber sealing portion. The thickness T2 is preferably chosen so that the sealing members 114, 116 have sufficient stiffness to substantially maintain their shape when the flushing chamber 150 is under positive pressure. This way, chamber sealing portions 180 and catheter sealing portions 182 are shaped to form seal interfaces, even when the flushing chamber is under positive pressure. As discussed in further detail below, the thickness T3 is preferably chosen so that the thinned regions 192 resiliently conform to the shape of the catheter when the flushing chamber 150 is under positive pressure.

As shown in FIG. 7, when the cleaning device 110 is closed, it is configured to receive fluid (e.g., liquid, such as saline) from a source of flushing fluid. The fluid flows into the flushing chamber 150 along a fluid flow path F. The fluid flow path F initially passes through the inlet port 152 in a direction orthogonal to the seal interface between the flat engagement surfaces 184 of the chamber sealing portions 180 of the sealing members 114, 116. The seal openings 170 of the sealing members 114, 116 are generally aligned with the fluid flow path F so that the fluid passes through the seal openings and fills the flushing chamber 150 both beneath the lower sealing member 116 (i.e., between the pressure surface 188 of the chamber sealing portion 180 thereof and the recessed lower chamber surface 138) and above the upper sealing member 114 (i.e., between the pressure surface 188 of the chamber sealing portion 180 thereof and the recessed upper chamber surface 136).

As indicated by the fluid flow path direction F, when the flushing chamber 150 is filled with fluid, the pressure of the fluid in the chamber applies a downward force on the pressure surface 188 of the chamber sealing portion 180 of the upper sealing member 114 and an upward force on the pressure surface of the chamber sealing portion of the lower sealing member 116. The pressure surfaces 188 are oriented so that a threshold positive fluid pressure exerts a force thereupon that is generally normal the seal interface formed therebetween and is suitable to urge the upper and lower sealing members 114, 116 toward one another and enhance the tightness of the seal interface between the flat engagement surfaces 184 of the upper and lower sealing members. It is contemplated that in other embodiments only one sealing member may have a pressure surface exposed to fluid pressure that acts on the pressure surface to enhance the tightness of a seal interface for sealing a flushing chamber without departing from the scope of the invention. In the illustrated embodiment, the inner portions 174 of the sealing members 114, 116, which are thinner than the outer border portions 172, extend into the flushing chamber 150. As a result, the chamber sealing portions 180 of the sealing members 114, 116, are more responsive to positive pressures in the flushing chamber 150 than they would be if the inner portions 174 were the same thickness as the outer border portions 172.

It is contemplated that the inner perimeter ends of the sealing members 114, 116 could be chamfered so that the force exerted thereupon by the positive fluid pressure in the flushing chamber is oriented in a direction that urges the sealing members toward one another, even at the extremities of the inner perimeter ends. This may be useful to prevent the sealing members 114, 116 from buckling, causing the seal interface formed by the chamber sealing portions 180 to break and resulting in a loss of pressure in the flushing chamber.

Referring to FIGS. 8 and 9, as indicated by the fluid flow path direction F, when the fluid in the flushing chamber 150 reaches a threshold positive pressure, it applies a generally downward force on the pressure surface 190 of the catheter sealing portion 182 of the upper sealing member 114 and a generally upward force on the pressure surface of the catheter sealing portion of the lower sealing member. The pressure surfaces 190 are oriented so that the positive fluid pressure exerts a force thereupon that is suitable to urge the catheter sealing portions 182 toward the catheter 10 and enhance the tightness of the seal interface between the concave surfaces 186 of the upper and lower sealing members 114, 116 and the catheter. The thinned regions 192 of the catheter sealing portions 182 are more pressure-responsive than the thicker regions of the upper and lower sealing members 114, 116. As a result, the tightness of the seal interface between the concave surfaces 186 and the catheter 10 is enhanced more greatly at the thinned regions 192 of the catheter sealing portions 182 than at thicker regions of the catheter sealing portions. Moreover, the thicker regions of the upper and lower sealing members 114, 116 are more stiff than the thinned regions 192 to resist damage and maintain the shape of the seal for proper interface with the catheter 10.

As shown in FIG. 6, the cleaning device 110 is configured to receive the catheter 10 so that the proximal opening 32 is disposed within the flushing chamber 150 and the distal opening 34 is disposed outside of the flushing chamber when the cleaning device is closed. The cleaning device 110 includes an alignment plate 194 for use in visually positioning the catheter 10 in the desired position relative the opposite longitudinal ends of the device body 112. As shown in FIG. 3, the alignment plate 194 includes a catheter tip indicator that illustrates an outline of the shape of the catheter 10. When the cleaning device 110 is viewed from above, the catheter 10 is positioned so that the tip of the catheter is generally aligned with the catheter tip indicator of the alignment plate 194. When the catheter tip aligns with the catheter tip indicator, the catheter 10 is positioned so that the proximal opening 32 is positioned within the flushing chamber 150 and the distal opening 34 is positioned outside of the flushing chamber when the device 110 is closed.

As shown in FIG. 6, when the fluid fills the flushing chamber 150 with the catheter 10 secured between the upper and lower body portions 118, 120 so that the proximal opening 32 is located within the flushing chamber and the distal opening 34 is located outside of the flushing chamber, the fluid flows along a flow path F into the proximal opening 32 (and other openings, e.g., micron-sized openings, disposed between the proximal opening 32 and distal opening 34), through the catheter lumen 30, and out the distal opening 34. If debris contained in the catheter lumen 30 occludes the lumen so that fluid cannot flow freely through the catheter lumen, the pressure in the flushing chamber 150 builds as fluid continues to flow into the chamber along the flow path F. As the pressure builds in the flushing chamber, it simultaneously increases the flushing force applied against the debris in the catheter lumen 30 and enhances the tightness of the seal interfaces formed between the chamber sealing portions 180 of the upper and lower sealing members 114, 116 and the catheter sealing portions 182 of the upper and lower sealing members and the catheter 10. As a result, if very high pressures are needed to dispel debris from the catheter lumen 30, the flushing chamber 150 can contain flushing fluid at the high pressure without leaking. Once the force applied against the debris in the catheter lumen 30 reaches a sufficiently high amount, the debris is flushed out of the distal opening 34 along with the fluid.

Figure 11:
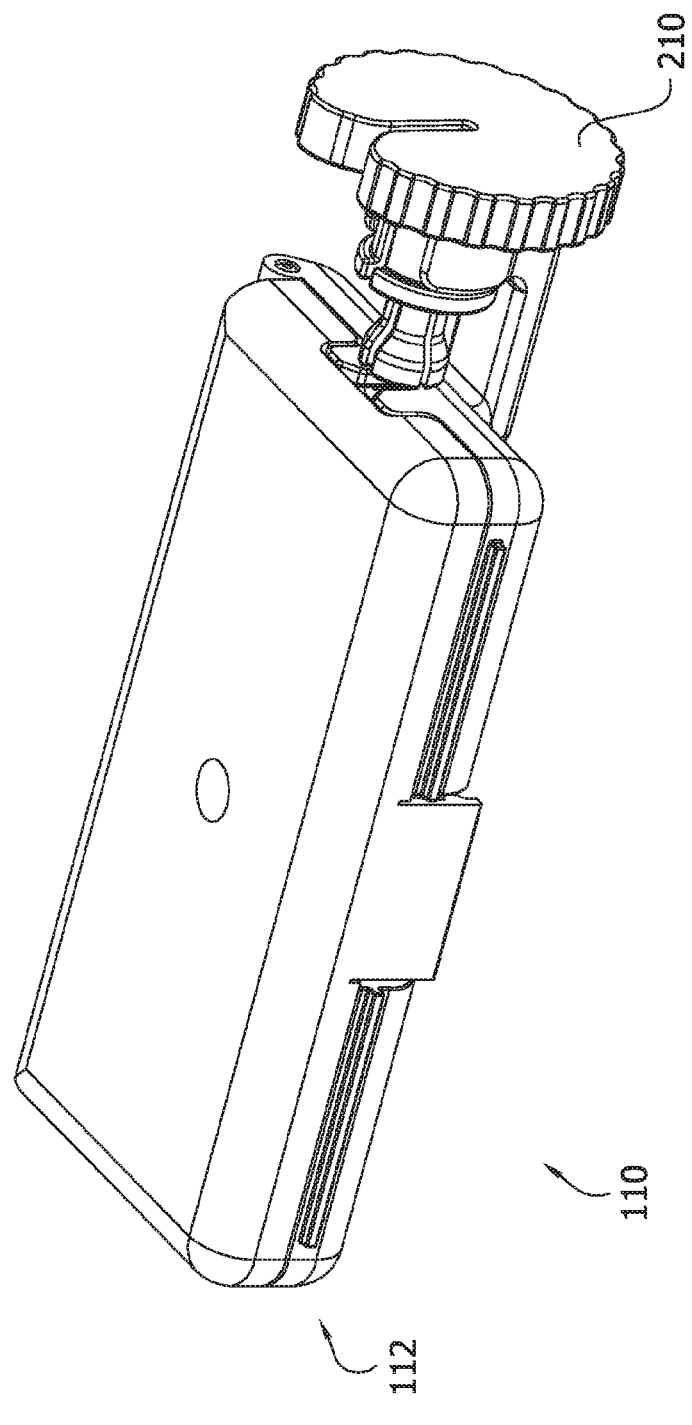
FIG. 11 is a perspective of the cleaning device including an opening/closing device for use in opening and closing the distal opening of the catheter.

As shown in FIG. 11, in lieu of the alignment plate 194, the cleaning device 110 can include a collet positioner 210 (broadly, an opening/closing device) rotatable secured to the lower body portion 120. To properly align the catheter relative the longitudinal ends of the cleaning device body 112, the distal tip 40 of the catheter 10 is inserted in the collet positioner 210. The collet positioner 210 grips the distal tip 40 of the catheter 10 so that rotation of the collet positioner 210 imparts rotation of the distal tip 40 relative to the catheter body 12 to open/close the distal opening 34.

Referring to FIG. 3, in one embodiment of a method of using the cleaning device 110, a user opens the device body 112 so that the upper and lower body portions 118, 120 thereof are in the open position. Using, for example, the alignment plate 194 or the collet positioner 210, the user positions the catheter 10 in the proper position relative the longitudinal ends of the device body 112. More specifically, the user positions the catheter 10 so it is received in the loose fit guides 146 and is secured in place in the snap-fit guides 148. The snap-fit guides 148 and the loose fit guides 146 align the catheter 10 properly relative the opposite sides of the device body 112. Preferably, the catheter 10 is secured to the cleaning device 110 so that, when the cleaning device is closed, the proximal opening 32 is positioned within the flushing chamber 150 and the distal opening 34 is outside of the flushing chamber. In one or more embodiments, the catheter 10 is secured to the cleaning device 110 while the catheter body 12 is connected to a guide wire. Thus, the cleaning device 110 can be used to flush debris from the catheter lumen 30 without removing the catheter 10 from the guide wire.

Subsequently, the cleaning device 110 is closed as shown in FIG. 4. Preferably, the clip 154 lockingly engages the lower body portion 120 to secure the device body 112 in the closed position. As shown in FIGS. 6-9, when the cleaning device 110 is closed, the inner faces 124, 126 of the upper and lower sealing members 114, 116 abut one another in opposing relationship. The flat engagement surfaces 184 of the chamber sealing portions 180 engage one another to form a seal interface therebetween. Likewise, the concave surfaces 186 of the catheter sealing portions 182, which are supported in the flushing chamber 150 by the seal supports 144, sealingly engage the catheter 10 adjacent proximal and distal ends of the chamber. Even in the absence of a positive fluid pressure in the flushing chamber 150, the sealing members 114, 116 form sealing interfaces that fluidly seal the flushing chamber.

A fluid source (not shown) is fluidly connected to the inlet port 152, and fluid is dispensed therefrom. The fluid flows through the inlet port 152 and into the flushing chamber 150 along the flow path F. Inside the flushing chamber 150, the fluid creates a positive pressure. The positive pressure in the flushing chamber 150 acts on the pressure surfaces 188 of the chamber sealing portions 180 of the upper and lower sealing members to urge the chamber sealing portions toward one another, thereby enhancing the tightness of the seal interface between the flat engagement surfaces 184. Likewise, the positive pressure in the flushing chamber 150 acts on the pressure surfaces 190 of the catheter sealing portions 182 to urge the catheter sealing portions thereof toward the catheter body 12, thereby enhancing the tightness of the seal interface between the arcuate surfaces 186 and the catheter body. The thinned regions 192 of the catheter sealing portions 182 are more responsive to the fluid pressure than thicker portions of the sealing members 114, 116 disposed within the flushing chamber 150, which ensures a fluid tight seal between the catheter 10 and the sealing members.

As shown in FIG. 6, some of the fluid in the flushing chamber 150 flows into the proximal opening 32, through the catheter lumen 30 (and any micron-shaped openings), and out the distal opening 34 of the catheter 10. If tissue and/or debris occludes the catheter lumen 30, the pressure increases in the pressure chamber 50 to increase the force applied against the tissue/debris by the fluid flow F until the fluid pressure overcomes the frictional force of the tissue/debris in the catheter lumen 30 and flushes the tissue/debris out of the lumen through the distal opening 34. Because the sealing members 114, 116 are arranged to enhance the tightness of the seal interfaces that seal the flushing chamber 150 when the flushing chamber is pressurized, high fluid pressures can be used to flush tissue/debris from the catheter lumen 30 without leaking.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A cleaning device for cleaning a medical instrument having a distal end portion defining an instrument lumen, the cleaning device comprising:
  a device body comprising first and second body portions having respective inner faces, the first and second body portions being movable relative to one another between a closed position, in which the inner faces are generally abutting and in opposing relationship with respect to one another, and an open position, in which the inner faces are spaced apart such that the medical instrument is receivable between the inner faces, the respective inner faces of the first and second body portions defining an internal flushing chamber of the device body when the first and second body portions are in the closed position;

an inlet port in fluid communication with the flushing chamber and configured to fluidly connect a source of fluid to the flushing chamber;

first and second sealing members secured to the inner faces of the respective first and second body portions, the first and second sealing members including respective first and second chamber sealing portions having respective first and second sealing surfaces adapted to engage one another to form a seal interface therebetween when the first and second body portions are in the closed position, wherein the first chamber sealing portion extends into the flushing chamber and has a first pressure surface opposite the first sealing surface and exposed to fluid pressure within the flushing chamber to enhance tightness of the seal interface when a positive fluid pressure is present in the flushing chamber.

2. The cleaning device set forth in claim 1, wherein the first pressure surface of the first chamber sealing portion is configured such that positive fluid pressure exerted on the first pressure surface in the flushing chamber is generally normal to the seal interface.

3. The cleaning device set forth in claim 1, wherein the flushing chamber is partially defined by a first chamber surface of the first body portion, wherein the first chamber sealing portion is spaced apart from the first chamber surface when the first and second body portions are in the closed position.

4. The cleaning device set forth in claim 1, wherein the second chamber sealing portion extends into the flushing chamber and has a second pressure surface opposite the second sealing surface and exposed to fluid pressure within the flushing chamber to enhance tightness of the seal interface when a threshold positive fluid pressure is present in the flushing chamber.

5. The cleaning device set forth in claim 4, wherein the first pressure surface is configured such that positive fluid pressure exerted on the first surface in the flushing chamber is generally normal to the seal interface, and wherein the second pressure surface is configured such that positive fluid pressure exerted on the second surface in the flushing chamber is generally normal to the seal interface.

6. The cleaning device set forth in claim 5, wherein the flushing chamber is partially defined by an upper chamber surface of the first body portion and a lower chamber surface of the second body portion, wherein the first and second chamber sealing portions are spaced apart from the respective upper and lower chamber surfaces when the first and second body portions are in the closed position.

7. The cleaning device set forth in claim 6, wherein each of the first and second sealing members has an inner portion extending inward around an entire perimeter of the flushing chamber into the flushing chamber when the first and second body portions are in the closed position.

8. The cleaning device set forth in claim 7, wherein the inner portion of each of the first and second sealing members has an inner periphery defining a seal opening in communication with the inlet port when the first and second body portions are in the closed position.

9. The cleaning device set forth in claim 8, wherein the inlet port is adapted to deliver fluid into the flushing chamber along a fluid flow path which is generally orthogonal to the seal interface when the first and second body portions are in the closed position.

10. The cleaning device set forth in claim 9, wherein the fluid flow path is generally aligned with the seal opening.

11. The cleaning device set forth in claim 1, wherein the first and second sealing members further include respective first and second instrument sealing portions configured to engage the medical instrument and form a seal interface therewith.

12. The cleaning device set forth in claim 11, wherein each of the first and second instrument sealing portions include proximal and distal sealing portions configured to form proximal and distal seal interfaces with the medical instrument.

13. The cleaning device set forth in claim 11, wherein the first and second sealing members are disposed within the flushing chamber when the first and second body portions are in the closed position.

14. The cleaning device set forth in claim 13, further comprising first and second instrument seal supports supporting the first and second instrument sealing portions in the flushing chamber when the first and second body portions are in the closed position.

15. A cleaning device for cleaning a medical instrument having a distal end portion defining an instrument lumen, the cleaning device comprising:

a device body comprising first and second body portions having respective inner faces, the first and second body portions being movable relative to one another between a closed position, in which the inner faces are generally abutting and in opposing relationship with respect to one another, and an open position, in which the inner faces are spaced apart such that the medical instrument is receivable between the inner faces, the respective inner faces of the first and second body portions defining respective first and second flushing cavities together defining an internal flushing chamber of the device body when the first and second body portions are in the closed position;

an inlet port in fluid communication with the flushing chamber and configured to fluidly connect a source of fluid to the flushing chamber;

first and second sealing members secured to the inner faces of the respective first and second body portions, the first and second sealing members including respective first and second chamber sealing portions having respective first and second sealing surfaces adapted to engage one another to form a seal interface therebetween when the first and second body portions are in the closed position, wherein the first and second chamber sealing portions extend over portions of the respective first and second flushing cavities such that pressurized fluid in the flushing chamber imparts forces on the first and second chamber sealing portions that urge the first and second sealing surfaces together.

16. The cleaning device set forth in claim 15, wherein the first and second chamber sealing portions have respective first and second pressure surfaces opposite the respective first and second sealing surfaces and exposed to fluid pressure within the flushing chamber to enhance tightness of the seal interface when a positive fluid pressure is present in the flushing chamber.

17. The cleaning device set forth in claim 16, wherein the first pressure surface is configured such that positive fluid pressure exerted on the first surface in the flushing chamber is generally normal to the seal interface, and wherein the second pressure surface is configured such that positive fluid pressure exerted on the second surface in the flushing chamber is generally normal to the seal interface.

18. The cleaning device set forth in claim 15, wherein the first and second sealing members further include respective first and second instrument sealing portions configured to engage the medical instrument and form a seal interface therewith.

19. The cleaning device set forth in claim 18, wherein each of the first and second instrument sealing portions include proximal and distal sealing portions configured to form proximal and distal seal interfaces with the medical instrument.

20. The cleaning device set forth in claim 15, wherein the first and second body portions are connected to one another by a hinge for moving the first and second body portions between the open and closed positions.

* * * * *